(12) United States Patent
Bonaventure et al.

(10) Patent No.: US 6,692,538 B2
(45) Date of Patent: Feb. 17, 2004

(54) USE OF NOVEL INDOLE COMPOUNDS FOR DYEING AND MAKING UP KERATIN MATERIALS, COMPOSITIONS COMPRISING THEM AND DYEING PROCESSES

(75) Inventors: Nicole Bonaventure, Vincennes (FR); Patrick Gilard, Villepinte (FR); Gilles Barre, Villepinte (FR); Michel Dubois, Pommeuse (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 10/137,397

(22) Filed: May 3, 2002

(65) Prior Publication Data

US 2003/0187277 A9 Oct. 2, 2003

Related U.S. Application Data

(62) Division of application No. 09/666,465, filed on Sep. 20, 2000, now Pat. No. 6,407,260.

(30) Foreign Application Priority Data

Sep. 22, 1999 (FR) .............................. 99 11833

(51) Int. Cl.$^7$ ................................. A61K 7/13
(52) U.S. Cl. ...................... 8/405; 8/409; 8/423; 8/421; 548/416; 548/417; 548/418; 548/486; 548/371.6
(58) Field of Search ............................ 8/405, 409, 423, 8/421; 548/484, 371.4, 416, 417, 418

(56) References Cited

U.S. PATENT DOCUMENTS

| | | | |
|---|---|---|---|
| 4,961,754 A | 10/1990 | Grollier | 8/423 |
| 5,112,360 A | 5/1992 | Garoche et al. | 8/406 |
| 5,468,872 A | 11/1995 | Glicksman et al. | 548/416 |
| 5,616,724 A * | 4/1997 | Hudkins et al. | 548/417 |
| 5,690,697 A | 11/1997 | Samain | 8/423 |
| 5,695,747 A | 12/1997 | Forestier et al. | 424/59 |
| 5,704,948 A | 1/1998 | Terranova et al. | 8/409 |
| 5,752,982 A | 5/1998 | Lang et al. | 8/409 |
| 5,755,829 A | 5/1998 | Terranova et al. | 8/409 |
| 5,938,792 A | 8/1999 | Lang et al. | 8/409 |
| 6,002,018 A | 12/1999 | Terranova et al. | 548/484 |
| 6,099,593 A | 8/2000 | Terranova et al. | 8/409 |
| 6,118,008 A | 9/2000 | Malle et al. | 548/371.4 |
| 6,203,580 B1 | 3/2001 | Vandenbossche et al. | 8/421 |
| 6,309,426 B1 | 10/2001 | Dias et al. | 8/407 |

FOREIGN PATENT DOCUMENTS

| | | |
|---|---|---|
| EP | 1086951 A1 | 3/2001 |
| FR | 2 618 069 | 1/1989 |

OTHER PUBLICATIONS

Paola Manini et al., "Acid–Promoted Competing Pathways in the Oxidative Polymerization of 5,6–Dihydroxyindoles and Related Compounds: Straightforward Cycotrimerization Routes to Diindolocarbazole Derivatives", J. Org. Chem. 63:7002–7008 (1998).

* cited by examiner

Primary Examiner—Yogendra N. Gupta
Assistant Examiner—Eisa Elhilo
(74) Attorney, Agent, or Firm—Finnegan, Henderson, Farabow, Garrett & Dunner, LLP

(57) ABSTRACT

The invention relates to the use of novel indole compounds as direct dyes in compositions intended for dyeing keratin materials, and, for example, compositions intended for dyeing human keratin fibers and including the hair, and in cosmetic compositions intended for making up the skin, the nails and the lips, to the dye compositions or make-up compositions comprising them and to the direct dyeing process using them, and processes of manufacturing said novel indole compounds.

75 Claims, No Drawings

USE OF NOVEL INDOLE COMPOUNDS FOR DYEING AND MAKING UP KERATIN MATERIALS, COMPOSITIONS COMPRISING THEM AND DYEING PROCESSES

This is a division of application Ser. No. 09/666,465 filed September 20, 2000 now U.S. Pat. No. 6,407,260, which is incorporated herein by reference.

The invention relates to novel indole compounds, to their use as direct dyes in compositions intended for dyeing keratin materials and for example compositions intended for dyeing human keratin fibres and including the hair, and in cosmetic compositions intended for making up the skin, the nails and the lips, to the dye compositions and make-up compositions comprising them and to the corresponding direct dyeing process.

In the field of hair dyeing, direct dyes are sought, i.e. dyes which, without supplying an oxidizing agent, are capable by themselves of temporarily modifying the natural shade of the hair. In this application, the dyes may satisfy a certain number of criteria, and for example they may generate rich and varied shades making it possible to obtain a wide range of colours likely to satisfy the formulator; in this perspective, novel compounds are always being sought to be able to dye in a range of colours extending for example from orange to red. Moreover, the dyeing results obtained may be reproducible, strong and resistant to washing, rubbing, permanent-waving, light and perspiration.

The inventors have now discovered, entirely surprisingly and unexpectedly, novel indole compounds of formula (I) defined below, in the range of shades from orange to red, which are suitable for use as direct dyes in the dyeing of keratin materials, and in make-up compositions for the skin, the nails and the lips.

These novel dyes can also make it possible to obtain strong orange to red shades which show excellent properties of resistance to one or more of the various treatments to which keratin fibres may be subjected, and for example the hair, with respect to light, washing, permanent-waving and perspiration.

These discoveries form the basis of the present invention.

A first subject of the invention is thus a novel compound of formula (I):

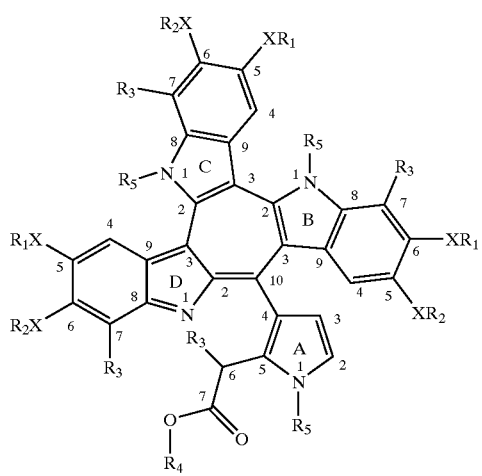

(I)

wherein:
X, which may be identical or different, are each chosen from oxygen atoms and nitrogen atoms;

$R_1$ and $R_2$, which may be identical or different, are each chosen from hydrogen atoms, $C_1$–$C_4$ alkyl groups, $C_1$–$C_4$ monohydroxyalkyl groups, $C_1$–$C_4$ polyhydroxyalkyl groups, acyl($C_1$–$C_4$ alkyl carbonyl) groups, $C_1$–$C_4$ aminoalkyl groups, $C_1$–$C_4$ polyaminoalkyl groups and $C_1$–$C_4$ aminohydroxyalkyl groups;

$R_3$, $R_4$ and $R_5$, which may be identical or different, are each chosen from hydrogen atoms and linear and branched, saturated and unsaturated $C_1$–$C_4$ hydrocarbons.

In formula (I) according to the invention, said alkyl groups are chosen from linear groups and branched groups and include, for example, methyl groups, ethyl groups, n-propyl groups, isopropyl groups, n-butyl groups, isobutyl groups and tert-butyl groups; said $C_1$–$C_4$ monohydroxyalkyl groups include, for example, —$CH_2$—$CH_2OH$ groups and said $C_1$–$C_4$ polyhydroxyalkyl groups include, for example, —CHOH—$CH_2OH$ groups.

Among the indole compounds of formula (I), the compound of formula (II) is an example:

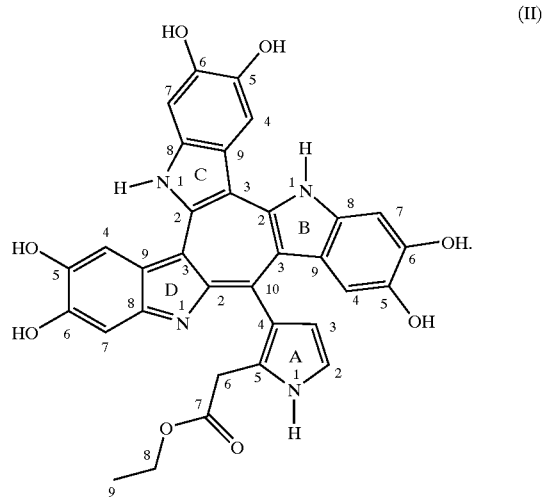

(II)

A subject of the invention is also a process for manufacturing an indole compound of formula (I) according to the invention comprising oxidation of the corresponding indole in a solvent medium according to oxidation processes that are generally well known to those skilled in the art.

In this way, a compound of formula (III):

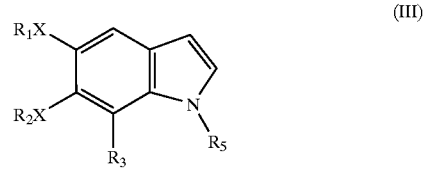

(III)

wherein $R_1$, $R_2$, $R_3$, $R_5$ and X have the same meanings as defined in formula (I) above, may be oxidized in alcoholic medium (methanol, ethanol, n-propanol, isopropanol, n-butanol and tert-butanol, for example). Additionally, said oxidation may be at room temperature. Further additionally, said oxidation may occur in the presence of sodium metaperiodate, to give a compound of formula (I) according to the invention.

Said sodium metaperiodate may also be replaced with appropriate sodium metaperiodate substitutes. Said substitutes may be chosen from, for example, molecular oxygen, hydrogen peroxide, potassium permanganate, selenium oxide and peracids. Said sodium metaperiodate and said appropriate substitutes may also be in the presence of metal catalysts which may be chosen from, for example, manganese, iron and chromium.

A subject of the invention is also a process for manufacturing an indole compound of formula (I) according to the invention, comprising oxidation of a compound of formula (III) described above in an alcoholic medium, in the presence of sodium metaperiodate, and at room temperature.

A subject of the invention is also a process of manufacturing a direct dye comprising including in said dyes at least one composition comprising at least one of said indole compounds of formula (I) according to the invention.

A subject of the invention is also a process of manufacturing make-up products comprising including in said make-up products at least one composition comprising at least one of said indole compounds of formula (I) according to the invention.

A subject of the invention is also a direct dye composition for keratin materials, comprising a medium suitable for dyeing and an effective amount of at least one compound of formula (I) according to the invention.

A subject of the invention is also a make-up product composition for keratin materials, comprising a medium suitable for make-up products and an effective amount of at least one compound of formula (I) according to the invention.

For the purposes of the present invention, the expression "keratin materials" mainly means the skin of the face and the body, the lips, the nails, at least one human keratin fiber such as human hair, body hairs, eyelashes and eyebrows, and also at least one keratin fiber such as natural textile fibers, including wool.

A subject of the invention is, for example, a direct dye composition for human keratin fibers such as the hair, comprising a medium suitable for dyeing and an effective amount of at least one compound of formula (I) according to the invention.

However, other non-limiting characteristics, aspects and advantages of the invention will emerge even more clearly on reading the description which follows, as well as the various concrete, but in no way limiting, examples intended to illustrate it.

When said composition is intended for dyeing, the compound(s) of formula (I) according to the invention can be each chosen from a range from approximately 0.05% to approximately 10% by weight relative to the total weight of the dye composition, and also from a range from approximately 0.05% to approximately 0.5% by weight relative to this weight.

When said composition is intended for make-up, the compound(s) of formula (I) according to the invention can be each chosen from a range from approximately 0.05% to approximately 20% by weight relative to the total weight of said composition, and also from a range from approximately 0.05% to approximately 5% by weight relative to this weight.

The compounds of formula (I) according to the invention can also serve, in well-known processes of oxidation dyeing of human keratin fibers, using oxidation dyes (oxidation dye precursors and optionally couplers), to shade the dyeing results obtained with the oxidation dyes or to enrich them with glints.

The dye composition according to the invention can also comprise, to broaden the range of shades and to obtain varied colours, besides the orange to red compounds of formula (I) according to the invention, other direct dyes conventionally used, for example nitrobenzene dyes, such as nitrophenylenediamines, nitrodiphenylamines, nitroanilines, nitrophenol ethers and nitrophenols, nitropyridines, anthraquinone dyes, monoazo dyes, diazo dyes, triarylmethane, azine, acridine and xanthene dyes, and alternatively metalliferous dyes.

The proportion of other additional said direct dyes can range from approximately 0.5% to approximately 10% by weight relative to the total weight of the dye composition.

The medium which is suitable for dyeing (or support) may generally comprise water or of a mixture of water and at least one organic solvent to dissolve compounds which may not be sufficiently soluble in water. Organic solvents which can be added to said composition, for example, are $C_1$–$C_4$ lower alkanols such as ethanol and isopropanol; glycerol; glycols and glycol ethers such as 2-butoxyethanol, propylene glycol, propylene glycol monomethyl ether and aromatic alcohols such as benzyl alcohol and phenoxyethanol, similar products and mixtures thereof.

The medium which is suitable for dyeing (or support) may also comprise fatty substances such as oils and waxes.

The solvents may be present in proportions ranging from approximately 1% to approximately 70% by weight relative to the total weight of the dye composition, and also ranging from approximately 5% to approximately 40% by weight.

Fatty amides such as mono- and diethanolamides of acids derived from copra, of lauric acid and of oleic acid can also be added to said composition according to the invention, at concentrations ranging from approximately 0.05% to approximately 10% by weight.

Surfactants, including those that are well known in the state of the art, can also be added to said composition according to the invention. Surfactants may be chosen from, for example, anionic types, cationic types, nonionic types, amphoteric types and zwitterionic types and mixtures thereof. Surfactants can be added to said composition in a proportion ranging from approximately 0.1% to approximately 50% by weight and also can range from approximately 1% to approximately 20% by weight relative to the total weight of said composition.

Thickeners can also be added to said composition according to the invention, in a proportion ranging from approximately 0.2% to approximately 5% by weight relative to the total weight of said composition.

Said dye composition can also comprise common adjuvants, wherein said adjuvants may be chosen from, for example, antioxidants, fragrances, sequestering agents, dispersants, hair conditioners, preserving agents and opacifiers, as well as any other adjuvants commonly used in the dyeing of keratin materials.

A person skilled in the art may select optional additional compound(s) mentioned above, such that the advantageous properties intrinsically associated with the dye composition may not, or may not substantially, be adversely affected by the addition(s) envisaged.

Said dye composition intended for dyeing keratin fibers may have a pH ranging generally from approximately 3 to approximately 12, and can range from approximately 5 to approximately 11. Said pH can be adjusted to the desired value by means of acidifying agents and basifying agents commonly used in the dyeing of keratin fibers.

Said acidifying agents which may be chosen include, for example, inorganic and organic acids such as hydrochloric acid, orthophosphoric acid, sulphuric acid, carboxylic acids such as acetic acid, tartaric acid, citric acid and lactic acid, and sulphonic acids.

Said basifying agents which may be chosen include, for example, aqueous ammonia, alkaline carbonates, alkanolamines such as mono-, di- and triethanolamine and derivatives thereof, sodium hydroxide, potassium hydroxide and the compounds of formula (IV) below:

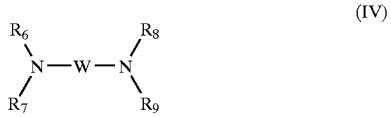

wherein
W is a propylene residue optionally substituted with groups chosen from hydroxyl groups and $C_1$–$C_6$ alkyl groups;
$R_6$, $R_7$, $R_8$ and $R_9$, which may be identical or different, are each chosen from hydrogen atoms, $C_1$–$C_6$ alkyl groups and $C_1$–$C_6$ hydroxyalkyl groups.

Dye compositions according to the invention can be in various forms, such as in the form of liquids, creams, gels and poultices, and in any other form which is suitable for dyeing keratin materials, and including human hair. For example, it can be packaged under pressure in an aerosol can in the presence of a propellant and can form a mousse.

Cosmetic compositions according to the invention intended for make-up may be chosen from, for example, make-up products for the face and the lips such as eyeshadows, face powders, powders and blushers, foundations, lipsticks and lip glosses and make-up products for the human body; they may also be make-up products for the eyelashes, the eyebrows and the nails, such as mascaras, eyebrow pencils, eyeliners and nail varnishes.

Another subject of the invention relates to a cosmetic process for treating at least one keratin fiber, for example human keratin fibers such as the hair and the nails, by direct dyeing, comprising applying to said at least one keratin fiber a composition comprising at least one compound of formula (I) according to the invention. In addition, said cosmetic process may include contact with wet or dry keratin fibers.

Said composition according to the invention can be used as a leave-in composition, i.e. after application of said composition to said fibers, said fibers may be dried without intermediate rinsing.

In other application methods, after applying said composition to said fibers for an exposure time ranging from approximately 3 to approximately 60 minutes, or ranging from approximately 5 to approximately 45 minutes, said fibers are rinsed, optionally washed and then rinsed again and dried.

Another subject of the invention relates to a composition for skin, for mucous membranes, or for keratin fibers comprising at least one compound of formula (I) according to the invention.

Another subject of the invention relates to a direct-dye composition comprising at least one compound of formula (I) according to the invention.

Another subject of the invention relates to a body hygiene composition; a hair composition; a make-up composition; a care composition; an anti-sun composition; or a self-tanning composition comprising at least one compound of formula (I) according to the invention.

Another subject of the invention relates to a composition for support comprising a medium suitable for support and at least one compound of formula (I) according to the invention.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result.

Concrete and non-limiting examples illustrating the invention will now be given.

PREPARATION EXAMPLE 1

To prepare the compound of formula (II) below:

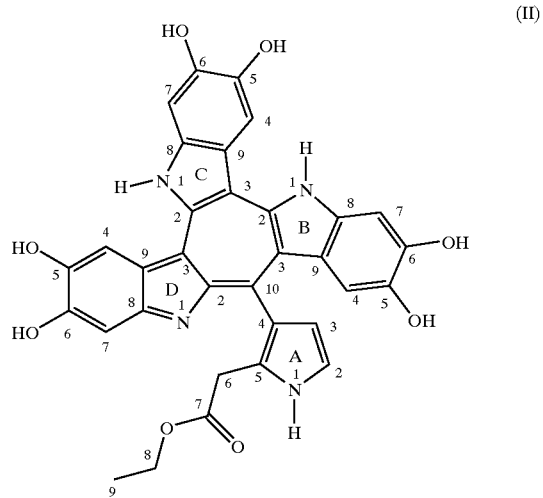

5 grams (0.033 mol) of 5,6-dihydroxyindole were dissolved in 100 grams of ethanol. 7.18 grams (0.033 mol) of sodium metaperiodate were added. The mixture was left stirring at room temperature for 8 hours. After centrifugation and washing, the organic phases were combined and evaporated to dryness.

The compound of formula (II) was isolated by preparative HPLC chromatography. After drying at 40° C., 50 mg of red crystals were isolated.

The structure of the compound was determined by $^1$H, $^{13}$C and $^{15}$N 1D NMR and by $^1$H-$^{13}$C and $^1$H-$^{15}$N 2D NMR and by mass spectrometry.

NMR: $^{13}$C NMR Spectrum (solvent: $CD_3OD$-$d_4$, reference: central signal of the solvent at 49.00 ppm): the $^{13}$C chemical shifts, the multiplicities (s: singlet, d: doublet, t: triplet, q: quartet) and the assignments are given in the table below:

| ¹³C chemical shifts | | |
|---|---|---|
| δ in ppm | Multiplicity | Assignment |
| 13.83 | q | C-9 A |
| 32.97 | t | C-6 A |
| 62.02 | t | C-8 A |
| 97.89 | d | C-7 D |
| 99.02 | d | C-7 B |
| 99.47 | d | C-7 C |
| 107.65 | d | C-4 D |
| 108.57 | d | C-4 C |
| 109.51 | d | C-3 A |
| 111.23 | d | C-4 B |
| 115.09 | s | C-3 C |
| 116.18 | s | C-3 D |
| 116.37 | s | C-9 D |
| 117.09 | s | C-9 C |
| 118.10 | s | C-9 B |
| 119.36 | s | C-4 A |
| 121.12 | d | C-2 A |
| 122.59 | s | C-5 A |
| 128.73 | s | C-3 B |
| 133.33 | s | C-10 A |
| 137.56 | s | C-5 B |
| 137.67 | s | C-5 C |
| 137.73 | s | C-5 D |
| 139.76 | s | C-2 D |
| 140.80 | s | C-2 C |
| 143.06 | s | C-2 B |
| 143.12 | s | C-6 B |
| 144.42 | s | C-6 C |
| 144.98 | s | C-6 D |
| 149.74 | s | C-8 B |
| 149.79 | s | C-8 C |
| 151.66 | s | C-8 D |
| 171.97 | s | C-7 A |

EXAMPLE 2 OF A DYE COMPOSITION

The direct dye composition below for hair was prepared:

| Compound of formula (II) | $10^{-3}$ mol | 0.6 g |
|---|---|---|
| Benzyl alcohol | | 14 g |
| Ethanol | | 46 g |
| Demineralized water | qs | 100 g |

The above composition was applied to locks of natural or permanent-waved grey hair containing 90% white hairs, at a rate of 5 g of composition per gram of hair, and was left to stand on the locks for 30 minutes. After rinsing with running water and drying, the hair was dyed in a deep red shade.

What is claimed is:

1. A composition comprising at least one compound of formula (I):

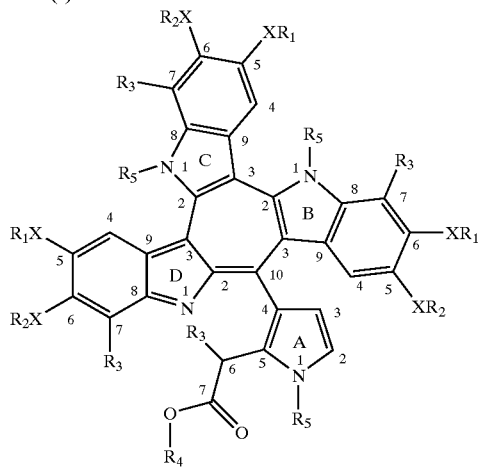

wherein:

X, which may be identical or different, are each chosen from oxygen atoms and nitrogen atoms;

$R_1$ and $R_2$, which may be identical or different, are each chosen from hydrogen atoms, $C_1$–$C_4$ alkyl groups, $C_1$–$C_4$ monohydroxyalkyl groups, $C_1$–$C_4$ polyhydroxyalkyl groups, acyl($C_1$–$C_4$ alkyl carbonyl) groups, $C_1$–$C_4$ aminoalkyl groups, $C_1$–$C_4$ polyaminoalkyl groups and $C_1$–$C_4$ aminohydroxyalkyl groups;

$R_3$, $R_4$ and $R_5$, which may be identical or different, are each chosen from hydrogen atoms and linear and branched, saturated and unsaturated $C_1$–$C_4$ hydrocarbons.

2. A composition according to claim 1, wherein said $C_1$–$C_4$ alkyl groups are chosen from methyl groups, ethyl groups, n-propyl groups, isopropyl groups, n-butyl groups, isobutyl groups and tert-butyl groups.

3. A composition according to claim 1, wherein said $C_1$–$C_4$ monohydroxyalkyl groups are —$CH_2$—$CH_2OH$ groups.

4. A composition according to claim 1, wherein said $C_1$–$C_4$ polyhydroxyalkyl groups are —CHOH—$CH_2OH$ groups.

5. A composition comprising the compound of formula (II):

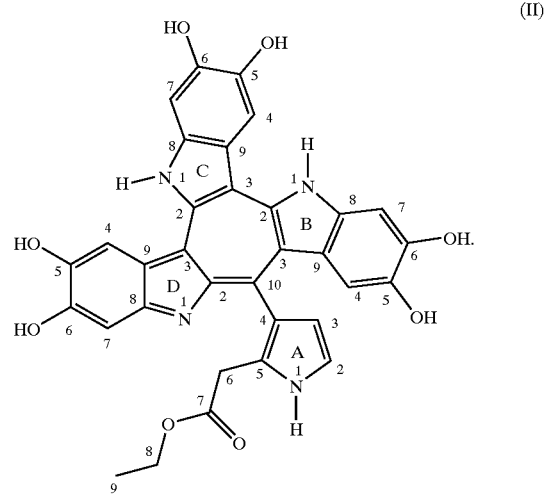

6. A composition according to claim 1, wherein said at least one compound of formula (I) is present in an amount ranging from 0.05% to 20% by weight relative to total weight of said composition.

7. A composition according to claim 6, wherein said at least one compound of formula (I) is present in an amount ranging from 0.05% to 10% by weight relative to total weight of said composition.

8. A composition according to claim 7, wherein said at least one compound of formula (I) is present in an amount ranging from 0.05% to 5% by weight relative to total weight of said composition.

9. A composition according to claim 8, wherein said at least one compound of formula (I) is present in an amount ranging from 0.05% to 0.5% by weight relative to total weight of said composition.

10. A composition according to claim 1, further comprising at least one additional direct dye.

11. A dye composition according to claim 10, wherein said at least one additional direct dye is chosen from nitrobenzene dyes, nitropyridine dyes, anthraquinone dyes, monoazo dyes, diazo dyes, triarylmethane dyes, azine dyes, acridine dyes, xanthene dyes and metalliferous dyes.

12. A composition according to claim 11, wherein said nitrobenzene dyes are chosen from nitrophenylenediamine dyes, nitrodiphenylamine dyes, nitroaniline dyes, nitrophenol ether dyes and nitrophenol dyes.

13. A composition according to claim 10, wherein said at least one additional direct dye is present in an amount ranging from about 0.5% to about 10% by weight relative to total weight of said composition.

14. A composition according to claim 1, further comprising a medium suitable for dyeing.

15. A composition according to claim 14, wherein said medium suitable for dyeing is chosen from water, water and at least one organic solvent, and at least one organic solvent.

16. A composition according to claim 15, wherein said organic solvents are present in an amount ranging from 1% to 70% by weight relative to the total weight of said composition.

17. A composition according to claim 16, wherein said organic solvents are present in an amount ranging from 5% to 40% by weight relative to the total weight of said composition.

18. A composition according to claim 15, wherein said organic solvents are chosen from $C_1$–$C_4$ lower alkanols, glycerol, glycols, glycol ethers and aromatic alcohols.

19. A composition according to claim 18, wherein said $C_1$–$C_4$ lower alkanols are chosen from ethanol and isopropanol.

20. A composition according to claim 18, wherein said glycols are chosen from propylene glycol.

21. A composition according to claim 18, wherein said glycol ethers are chosen from 2-butoxyethanol and propylene glycol monomethyl ether.

22. A composition according to claim 18, wherein aromatic alcohols are chosen from benzyl alcohol and phenoxyethanol.

23. A composition according to claim 14, wherein said medium suitable for dyeing further comprises at least one fatty substance.

24. A composition according to claim 23, wherein said at least one fatty substance is chosen from oils and waxes.

25. A composition according to claim 1, further comprising at least one fatty amide.

26. A composition according to claim 25, wherein said fatty amide is chosen from monoethanolamides and diethanolamides of acids derived from copra, monoethanolamides and diethanolamides of lauric acid, and monoethanolamides and diethanolamides of oleic acid.

27. A composition according to claim 25, wherein said fatty amide is present in an amount ranging from 0.05% to 10% by weight relative to the total weight of said composition.

28. A composition according to claim 1, further comprising at least one surfactant.

29. A composition according to claim 28, wherein said at least one surfactant is chosen from anionic, cationic, nonionic, amphoteric, and zwitterionic surfactants.

30. A composition according to claim 28, wherein said at least one surfactant is present in an amount ranging from about 0.1% to 50% by weight relative to the total weight of said composition.

31. A composition according to claim 30, wherein said at least one surfactant is present in an amount ranging from about 1% to 20% by weight relative to the total weight of said composition.

32. A composition according to claim 1, further comprising at least one thickener.

33. A composition according to claim 32, wherein said at least one thickener is present in an amount ranging from about 0.2% to 5% by weight relative to the total weight of said composition.

34. A composition according to claim 1, further comprising at least one adjuvant.

35. A composition according to claim 34, wherein said at least one adjuvant is chosen from antioxidants, fragrances, sequestering agents, dispersants, hair conditioners, preserving agents and opacifiers.

36. A composition according to claim 1, wherein said composition has a pH ranging from 3 to 12.

37. A composition according to claim 36, wherein said pH ranges from 5 to 11.

38. A composition according to claim 36, wherein said pH is obtained by including in said composition at least one agent chosen from acidifying agents and basifying agents.

39. A composition according to claim 38, wherein said acidifying agents are chosen from inorganic acids and organic acids.

40. A composition according to claim 39, wherein said inorganic acids are chosen from hydrochloric acid, orthophosphoric acid, and sulphuric acid.

41. A composition according to claim 39, wherein said organic acids are chosen from carboxylic acids and sulphonic acids.

42. A composition according to claim 41, wherein said carboxylic acids are chosen from acetic acid, tartaric acid, citric acid and lactic acid.

43. A composition according to claim 38, wherein said basifying agents are chosen from aqueous ammonia, alkaline carbonates, alkanolamines, sodium hydroxide, potassium hydroxide and compounds of formula (IV):

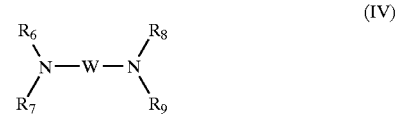

(IV)

wherein

W is a propylene residue optionally substituted with groups chosen from hydroxyl groups and $C_{1-C_6}$ alkyl groups; and $R_6$, $R_7$, $R_8$ and $R_9$, which may be identical or different, are each chosen from hydrogen atoms, $C_1$–$C_6$ alkyl groups and $C_1$–$C_6$ hydroxyalkyl groups.

44. A composition according to claim 43, wherein said alkanolamines are chosen from monoethanolamines, diethanolamines, triethanolamines and derivatives thereof.

45. A composition according to claim 1, wherein the composition is for skin, for mucous membranes, or for keratin fibers.

46. A composition according to claim 45, wherein said skin is chosen from skin of the face and skin of the body.

47. A composition according to claim 45, wherein said keratin fibers are chosen from nails, eyelashes, eyebrows, and hair.

48. A direct-dye composition comprising at least one compound of formula (I):

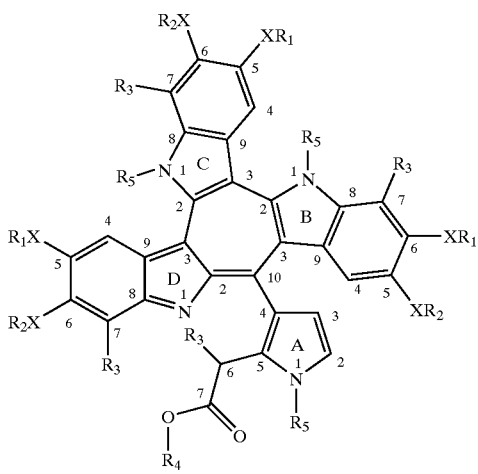

(I)

wherein:
X, which may be identical or different, are each chosen from oxygen atoms and nitrogen atoms;
$R_1$ and $R_2$, which may be identical or different, are each chosen from hydrogen atoms, $C_1$–$C_4$ alkyl groups, $C_1$–$C_4$ monohydroxyalkyl groups, $C_1$–$C_4$ polyhydroxyalkyl groups, acyl( $C_1$–$C_4$ alkyl carbonyl) groups, $C_1$–$C_4$ aminoalkyl groups, $C_1$–$C_4$ polyaminoalkyl groups and $C_1$–$C_4$ aminohydroxyalkyl groups;
$R_3$, $R_4$ and $R_5$, which may be identical or different, are each chosen from hydrogen atoms and linear and branched, saturated and unsaturated $C_1$–$C_4$ hydrocarbons.

49. A direct-dye composition according to claim 48, wherein said at least one compound of formula (I) is present in an amount ranging from 0.05% to 10% by weight relative to total weight of said composition.

50. A composition according to claim 1, wherein said composition is a dyeing composition; a body hygiene composition; a hair composition; a make-up composition; a care composition; an anti-sun composition; or a self-tanning composition.

51. A make-up composition according to claim 50, wherein said at least one compound of formula (I) is present in an amount ranging from 0.05% to 20% by weight relative to total weight of said composition.

52. A make-up composition according to claim 50, wherein said at least one compound of formula (I) is present in an amount ranging from 0.05% to 5% by weight relative to total weight of said composition.

53. A composition according to claim 50, wherein said body hygiene compositions are deodorant sticks.

54. A composition according to claim 50, wherein said hair compositions are chosen from hair styling sticks and hair make-up sticks.

55. A composition according to claim 50, wherein said make-up compositions are for skin of the face, for skin of the body, and for mucous membranes.

56. A composition according to claim 50, wherein said make-up compositions are chosen from eyeshadows, face powders, body powders, blushers, foundations, lipsticks, lip glosses, mascaras, eyebrow pencils, eyeliners and nail varnishes.

57. A composition according to claim 50, wherein said care compositions are for skin and mucous membranes.

58. A composition according to claim 50, wherein said care compositions are lipcare balms, lipcare bases, ointments for the body, and daily body care creams.

59. A method of manufacturing a direct dye comprising including in said dye at least one composition comprising at least one compound of formula (I):

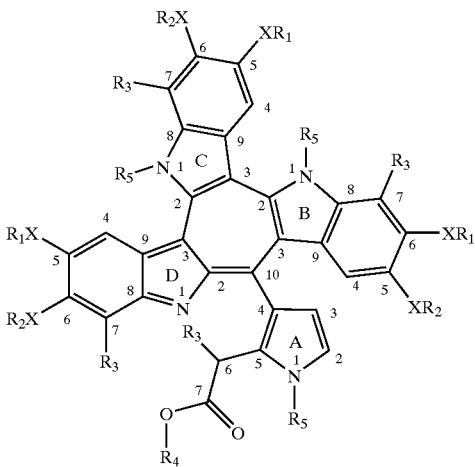

(I)

wherein:
X, which may be identical or different, are each chosen from oxygen atoms and nitrogen atoms;
$R_1$ and $R_2$, which may be identical or different, are each chosen from hydrogen atoms, $C_1$–$C_4$ alkyl groups, $C_1$–$C_4$ monohydroxyalkyl groups, $C_1$–$C_4$ polyhydroxyalkyl groups, acyl( $C_1$–$C_4$ alkyl carbonyl) groups, $C_1$–$C_4$ aminoalkyl groups, $C_1$–$C_4$ polyaminoalkyl groups and $C_1$–$C_4$ aminohydroxyalkyl groups;
$R_3$, $R_4$ and $R_5$, which may be identical or different, are each chosen from hydrogen atoms and linear and branched, saturated and unsaturated $C_1$–$C_4$ hydrocarbons.

60. A method of manufacturing a make-up product comprising including in said make-up product at least one composition comprising at least one compound of formula (I):

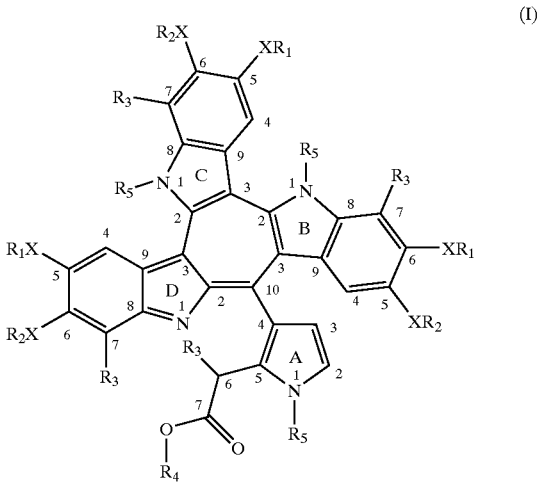

(I)

wherein:
X, which may be identical or different, are each chosen from oxygen atoms and nitrogen atoms;
$R_1$ and $R_2$, which may be identical or different, are each chosen from hydrogen atoms, $C_1$–$C_4$ alkyl groups, $C_1$–$C_4$ monohydroxyalkyl groups, $C_1$–$C_4$ polyhydroxyalkyl groups, acyl($C_1$–$C_4$ alkyl carbonyl) groups, $C_1$–$C_4$ aminoalkyl groups, $C_1$–$C_4$ polyaminoalkyl groups and $C_1$–$C_4$ aminohydroxyalkyl groups;

$R_3$, $R_4$ and $R_5$, which may be identical or different, are each chosen from hydrogen atoms and linear and branched, saturated and unsaturated $C_1$–$C_4$ hydrocarbons.

61. A process of direct dyeing at least one keratin fiber comprising contacting for a sufficient time said at least one keratin fiber with a composition comprising a sufficient amount of at least one compound of formula (I):

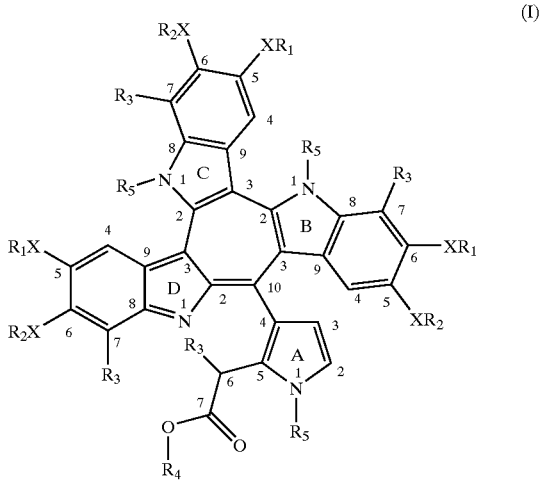

wherein:

X, which may be identical or different, are each chosen from oxygen atoms and nitrogen atoms;

$R_1$ and $R_2$, which may be identical or different, are each chosen from hydrogen atoms, $C_1$–$C_4$ alkyl groups, $C_1$–$C_4$ monohydroxyalkyl groups, $C_1$–$C_4$ polyhydroxyalkyl groups, acyl($C_1$–$C_4$ alkyl carbonyl) groups, $C_1$–$C_4$ aminoalkyl groups, $C_1$–$C_4$ polyaminoalkyl groups and $C_1$–$C_4$ aminohydroxyalkyl groups;

$R_3$, $R_4$ and $R_5$, which may be identical or different, are each chosen from hydrogen atoms and linear and branched, saturated and unsaturated $C_1$–$C_4$ hydrocarbons.

62. A process according to claim 61, wherein said at least one keratin fiber is chosen from human keratin fibers and natural fibers.

63. A process claim 62, wherein said human keratin fibers are chosen from skin of the face, skin of the body, the lips, the nails, hair, body hair, eyelashes, and eyebrows.

64. A process according to claim 62, wherein said natural fibers is wool.

65. A process according to claim 61, wherein said composition further comprises an oxidation compound.

66. A process according to claim 65, wherein said oxidation compound is chosen from oxidation dyes, oxidation precursor and oxidation couplers.

67. A process according to claim 61, wherein said composition further comprises at least one additional direct dye.

68. A process according to claim 67, wherein said at least one additional direct dye is chosen from nitrobenzene dyes, nitropyridine dyes, anthraquinone dyes, monoazo dyes, diazo dyes, triarylmethane dyes, azine dyes, acridine dyes, xanthene dyes and metalliferous dyes.

69. A process according to claim 68, wherein said nitrobenzene dyes are chosen from nitrophenylenediamine dyes, nitrodiphenylamine dyes, nitroaniline dyes, nitrophenol ether dyes and nitrophenol dyes.

70. A process according to claim 67, wherein said at least one additional direct dye is present in an amount ranging from about 0.5% to about 10% by weight relative to total weight of said composition.

71. A process according to claim 61, said at least one keratin fiber may be dried without intermediate rinsing.

72. A process according to claim 61, wherein said composition is in contact with said at least one keratin fiber for a time ranging from about 3 to 60 minutes.

73. A process according to claim 72, wherein said time ranges from about 5 to 45 minutes.

74. A process according to claim 61, further comprising rinsing said fibers after said sufficient time.

75. A process according to claim 74, further comprising washing said fibers after said rinsing, rinsing again, and then drying.

* * * * *